United States Patent
Mille et al.

(10) Patent No.: US 6,500,784 B1
(45) Date of Patent: Dec. 31, 2002

(54) HERBICIDAL COMPOSITIONS AND SURFACTANT CONCENTRATES

(75) Inventors: Fabien Hervé Joseph Mille, Commercy (FR); Philip James Oxford, London (GB)

(73) Assignee: Huntsman International LLC, West Midlands (GB)

( * ) Notice: Subject to any disclaimer, the term of this patent is extended or adjusted under 35 U.S.C. 154(b) by 0 days.

(21) Appl. No.: 09/868,881

(22) PCT Filed: Dec. 22, 1999

(86) PCT No.: PCT/EP99/10269

§ 371 (c)(1),
(2), (4) Date: Aug. 30, 2001

(87) PCT Pub. No.: WO00/38523

PCT Pub. Date: Jul. 6, 2000

(30) Foreign Application Priority Data

Dec. 23, 1998 (GB) ............................................. 9828258
Jan. 21, 1999 (GB) ............................................. 9901205

(51) Int. Cl.$^7$ ................................................ A01N 57/00
(52) U.S. Cl. ...................................... 504/206; 504/127
(58) Field of Search ........................... 504/116.1, 206, 504/127

(56) References Cited

U.S. PATENT DOCUMENTS 5,863,863 A * 1/1999 Hasebe et al. ............... 504/116
6,121,199 A * 9/2000 Berger et al. ............... 504/206

* cited by examiner

Primary Examiner—Alton Pryor
(74) Attorney, Agent, or Firm—Frishauf, Holtz, Goodman & Chick, P.C.

(57) ABSTRACT

A herbicidal aqueous solution comprising from 30% by weight, of said solution to saturation of a water soluble glyphosate salt; from 8 to 20% by weight of said solution is surfactant, said surfactant comprising from 10 to 100% by weight based on the total weight of said surfactant of an amphoteric surfactant; and from 30% to 90% by weight of ether carboxylate, based on the total weight of surfactant; said solution containing less than 0.035% of sodium ion.

14 Claims, No Drawings

HERBICIDAL COMPOSITIONS AND SURFACTANT CONCENTRATES

This application is a U.S. National Phase Application under 35 USC 371 of International Application PCT/EP99/10269 (published in English) filed Dec. 22, 1999.

The present invention relates to concentrated herbicidal compositions comprising water soluble glyphosate salts and a surfactant.

A number of formulations have been proposed whereby the herbicide N-(phosphonomethyl)glycine, alias glyphosate, may be supplied as a concentrated aqueous solution with a surfactant synergist which aids wetting and penetration, when the composition is diluted and applied to herbage.

Factors governing the choice of surfactant include wetting power, herbicidal or synergistic action, environmental profile and ability to form stable solutions with glyphosate at as high a concentration as possible, as well as cost.

The surfactant which have so far proved most cost effective for these purposes have been ethoxylated amines. The latter however have a poor environmental profile being biotoxic and poorly biodegradable. There is a demand for a more environmentally acceptable alternative to amine ethoxylates.

We have discovered that ether carboxylates meet most of the above criteria but are insufficiently soluble in concentrated glyphosate solutions. We have furthers noted that amphoteric surfactants also meet most of the above criteria and can act as cosurfactants, solubilising ether carboxylates, but solutions of commercial amphoteric surfactants in concentrated glyphosate are unstable and have been found to deposit crystals of glyphosate salts.

Amphoteric surfactants comprise betaines, sulpho betaines and phosphobetaines. However the great majority of the amphoteric surfactants sold commercially are betaines. The betaines of commerce are normally made by quaternising an amine by reaction with sodium chloracetate. This reaction forms sodium chloride as an unavoidable by-product. As a result commercial betaines contain about 6 to 12% of sodium chloride. We have now discovered that it is possible to use amphoteric surfactants at the required levels in glyphosate solution concentrates without instability, if the sodium chloride content is substantially reduced. Low salt betaines typically contain less than 3% preferably less than 2%, more preferably less than 1% e.g. less than 0.5% especially less than 0.2% sodium ion expressed as wt. sodium chloride based on the weight of surfactant.

The invention provides a herbicidal aqueous solution comprising from 30% by weight, to saturation of a water soluble glyphosate salt and from 8 to 20% by weight of surfactant comprising 10 to 100% by weight based on the total weight of surfactant of an amphoteric surfactant and from 0 to 90% by weight based on the total weight of surfactant of ether carboxylate, said solution containing less the 0.035% by weight of sodium ion.

Sodium ion may be removed from amphoteric surfactants, either by electrosmosis, e.g. as described in our GB 1 525 692 or in EP 0 736 521, or by membrane filtration, for example as described in EP 0 626 881, or, less preferably, by displacing sodium ion with, for example, potassium or ammonium, e.g. using ion exchange. Alternatively, it is possible to prepare betaines with low salt levels by quarternising with acrylic acid.

The glyphosate is preferably present as its potassium, ammonium, $C_2$ to $_3$ amine or mono or diethanolamine salt, or metho sulphate or as a mixture of two or more of said salts. Particularly preferred is the isopropylamine salt.

We prefer that the total level of inorganic salt be less than 0.39% by weight.

The amphoteric surfactant is preferably a betaine, e.g. a betaine of the formula: $RR^1{}_2N^+CH_2COO^-$, wherein R is an alkyl, alkenyl or alkyl phenyl group having an average of from 6 to 20, e.g. 8 to 14 aliphatic carbon atoms and $R^1$ is an alkyl or hydroxy alkyl group having an average of from 1 to 4 carbon atoms. Particularly preferred are the so called quaternary imidazoline betaines, also called ampho acetates, and commonly ascribed the formula:

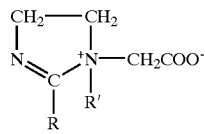

(although they are actually present predominantly as the corresponding non cyclic amido amine) wherein R and R' are alkyl, alkenyl, cycloalkyl, alkaryl or hydroxyalkyl groups having an average of from 1 to 20 aliphatic carbon atoms and R preferably has an average of from 6 to 20, e.g. 8 to 14 aliphatic carbon atoms and R' preferably has 1 to 4 carbon atoms. Other amphoteric surfactants for use according to our invention include alkyl amine polyalkoxy sulphates, sulphobetaines and other quaternary amine or quaternised imidazoline sulphonic acids and their salts, and Zwitterionic surfactants, e.g. N-alkyl taurines, carboxylated amido amines such as $RCONH(CH_2)_nN^+R'{}_2CH_2CO^-{}_2$ where n is 2 to 4, and amino acids having, in each case, hydrocarbon groups capable of conferring surfactant properties (e.g. alkyl, cycloalkyl alkenyl or alkaryl groups having from 6 to 20 aliphatic carbon atoms). Typical examples include 2-tallow alkyl, 1-tallow amido alkyl, 1-carboxymethyl imidazoline, 2-coconut alkyl N-carboxymethyl 2 (hydroxyalkyl) imidazoline, alkyl amido ethyl, propyl or butyl dimethyl betaine and $C_{6-20}$ alkyl dimethyl betaine. Generally speaking any water soluble amphoteric or Zwitterionic surfactant compound which comprises a hydrophobic portion including $C_{6-20}$ alkyl or alkenyl group and a hydrophilic portion containing an amine or quaternary ammonium group and a carboxylate, sulphate or sulphonic acid group may be used in our invention.

We particularly prefer short chain alkyl amido betaines, ampho acetates and alkyl betaines in which the alkyl group has 6 to 10 carbon atoms since they give very low foaming and permit high levels of ether carboxylate to be solubilised.

The surfactant preferably comprises at least 20% more preferably at least 30%, most preferably at least 40% e.g. 50 to 100% by weight of the amphoteric surfactant based on the total weight of surfactant.

We strongly prefer that the surfactant comprises an ether carboxylate. The ether carboxylate is preferably present in an amount of at least 10%, preferably more than 20% e.g. 30 to 60% by weight based on the total weight of surfactant. Generally the shorter the long alkyl chain of the betaines the higher the proportion of ether carboxylate that can be readily dissolved in a stable solution.

The ether carboxylate preferably has the formula $R(OCH_2CH_2)_nOCH_2CO_2^-$ wherein R is a straight or branched alkyl, alkenyl, alkylphenyl or polypropylene oxy group having from 6 to 20 e.g. 8 to 14 aliphatic carbon atoms and n is from 1 to 30, preferably, 2 to 20 e.g. 3 to 10.

The counter ion of the ether carboxylate may preferably comprise ammonium, potassium and or an amine or alkanolamine having up to six carbon atoms.

The surfactant may optionally but preferably comprise up to 20% by weight, e.g. 5 to 10% based on the total weight of surfactant, of a non-ionic wetting agent. The non-ionic wetting agent is preferably an ethoxylated alcohol such as a $C_6$ to $C_{25}$ straight or branched alkyl 1 to 30 mole ethoxylate e.g. a $C_{10}$ to $C_{18}$ alkyl 5 to 20 mole ethoxylate. The wetting agent gives better coverage of the leaf and superior herbicidal action.

We prefer that the surfactants should be pre-blended as a concentrate for supply to formulators of glyphosate compositions. To maintain sufficient mobility and to formulators of glyphosate compositions. To maintain sufficient mobility and dispersibility of such concentrates we prefer to add a suitable water miscible solvent such as a water miscible glycol or glycol ether, e.g. polyethylene glycol having a mean mol weight between 90 and 600 especially 130 to 250.

Such concentrates containing from 10 to 70% by weight ether carboxylate, from 20 to 80% by weight of low salt amphoteric surfactant and from 10 to 50% by weight of solvent are a further embodiment of the invention.

Preferably said concentrates additionally contain from 3 to 20% of a non-ionic wetting agent and/or from 1 to 6% of a sequestrant such as an aminophosphonate, e.g. of the formula.

$$(M_2PO_3CH_2)_2N[CH_2CH_2NCH_2PO_3M_2]_nCH_2PO_3M_2$$

where n is from 0 to 10 preferably 2 to 6 and M is a compatible cation to provide a water soluble product.

The formulation may typically contain from 1 to 3% of sequestrant.

The concentrates contain, typically less than 70% water, preferably less than 60% water most preferably 10 to 55% water by weight of the concentrate.

The invention will be illustrated by the following examples

EXAMPLE 1

A composition was prepared comprising 360 gl$^{-1}$ isopropylamine salt of glyphosate as acid equivalent and 105 gl$^{-1}$ active ingredient of $C_{12-14}$ alkyl betaine, as a 37% solution desalinated by electrosmosis to a sodium chloride level of less than 1%. The composition was a clear solution which was stable on storage in a cold incubator at 0° C. and at ambient temperature.

For comparison a composition was prepared as described above, but using as surfactant a commercial $C_{12-14}$ alkyl betaine sold under the Registered Trade Mark "EMPIGEN" BB and containing 6% sodium chloride. The comparative example was unstable and deposited crystals of glyphosate when stored in a cold incubator at 0° C. and after 2 to 3 weeks at ambient temperature.

EXAMPLE 2

The formulation of claim 1 was prepared using a desalinated coco imidazoline betaine and for comparison a commercial coco imidazoline betaine sold as a 38% solids aqueous solution containing 11% sodium chloride under the Registered Trade Mark "EMPIGEN" CDR60.

The former composition was stable on storage at 0° C. and at 54° C. The comparative example deposited crystals of glyphosate at both temperatures.

EXAMPLE 3

The formulation of example 1 was repeated using a desalinated coco amidopropyl betaine, and, as comparison a commercial equivalent sold as "EMPIGEN" BS containing 6.5% sodium chloride. The example was stable on storage at 0° C., but the comparative example deposited crystals of glyphosate at these temperatures.

EXAMPLE 4 to 16

The following compositions containing alkyl polyethoxymethyl carboxylates of the formula $R(OCH_2CH_2)_n OCH_2CO_2H$ where R and n are as defined below and the desalinated alkyl betaine of claim 1 were all stable at 0° C. for 1 week, and at 54° C. for two weeks and were fully soluble in water containing 500 ppm hardness.

The ether carboxylates were sold under the Registered Trade Mark "EMPICOL" and are identified as follows:

| | |
|---|---|
| "EMPICOL" CYJ | R = hexyl, n = 10 |
| "EMPICOL" CVE | R = capryl, n = 6 |
| "EMPICOL" CVH | R = capryl, n = 8 |
| "EMPICOL" CLI | R = oleyl, n = 10 |
| "EMPICOL" CED5 | R = lauryl, n = 6 |

EXAMPLE 4

| | |
|---|---|
| Glyphosate isopropylamine salt: | 360 g/l as acid equivalent |
| Polyethylene glycol (MW200) | 40 g/l |
| Desalinated alkyl betaine | 52.5 g/l as active matter |
| "EMPICOL" CYJ | 52.5 g/l as active matter |
| Ammonia | to pH 5 +/− 0.1 |
| Demineralised water | to 1 l or 1176 g |

The PEG betaine and ether carboxylate were mixed to form a stable concentrate. The latter was dispersed readily in the water with the glyphosate and ammonia.

EXAMPLE 5

As example 4 but replacing "EMPICOL" CYJ with "EMPICOL" CVE

EXAMPLE 6

As example 4 but replacing "EMPICOL" CYJ with "EMPICOL" CVH

EXAMPLE 7

As example 4 but replacing "EMPICOL" CYJ with "EMPICOL" CLI

EXAMPLE 8

| | |
|---|---|
| Glyphosate isopropylamine salt: | 360 g/l as acid equivalent |
| Polyethylene glycol | 40 g/l |
| Desalinated alkyl betaine | 75 g/l as active matter |
| "EMPICOL" CYJ | 75 g/l as active matter |
| Ammonia | to pH 5 +/− 0.1 |
| Demineralised water | to 1 l or 1176 g |

The PEG, ether carboxylate and betaine were mixed to form a stable concentrate which was easily dispersed in water with the glyphosate and ammonia.

EXAMPLE 9

As for example 8 replacing "EMPICOL" CYJ for "EMPICOL" CVE

EXAMPLE 10

As for example 8 replacing "EMPICOL" CYJ for "EMPICOL" CVH

EXAMPLE 11

| | |
|---|---|
| Glyphosate isopropylamine salt: | 360 g/l as acid equivalent |
| Polyethylene glycol | 40 g/l |
| Desalinated alkyl betaine | 42 g/l as active matter |
| "EMPICOL" CYJ | 63 g/l as active matter |
| Ammonia | to pH 5 +/− 0.1 |
| Demineralised water | to 1 l or 1176 g |

The PEG, betaine and ether carboxylate were mixed to form a stable concentrate which was easily dispersed in water with the glyphosate and ammonia.

EXAMPLE 12

As for example 11, replacing "EMPICOL" CYJ for "EMPICOL" CVE

EXAMPLE 13

As for example 11 replacing "EMPICOL" CYJ by "EMPICOL" CVH

EXAMPLE 14

| | |
|---|---|
| Glyphosate isopropylamine salt: | 360 g/l as acid equivalent |
| Polyethylene glycol (MW200) | 40 g/l |
| Desalinated alkyl betaine | 60 g/l as active matter |
| "EMPICOL" CVE | 90 g/l as active matter |
| Ammonia | to pH 5 +/− 0.1 |
| Demineralised water | to 1 l or 1176 g |

EXAMPLE 15

| | |
|---|---|
| Glyphosate isopropylamine salt: | 360 g/l as acid equivalent |
| Polyethylene glycol (MW200) | 40 g/l |
| Desalinated alkyl betaine | 60 g/l as active matter |
| "EMPICOL" CVH | 90 g/l as active matter |
| Ammonia | to pH 5 +/− 0.1 |
| Demineralised water | to 1 l or 1176 g |

EXAMPLE 16

| | |
|---|---|
| Glyphosate isopropylamine salt: | 360 g/l as acid equivalent |
| Polyethylene glycol (MW200) | 40 g/l |
| Desalinated cocoamidopropyl betaine of example 3 | 52.5 g/l as active matter |
| "EMPICOL" CVE | 52.5 g/l as active matter |
| Ammonia | to pH 5 +/− 0.1 |
| Demineralised water | to 1 l or 1176 g |

EXAMPLES 17 to 28

Examples 4 to 15 were repeated using a $C_8$ alkyl amidopropyl betaine. Stable concentrates and solutions exhibiting very low foaming were obtained.

EXAMPLES 29 to 53

Examples 4 to 28 were repeated with the addition of 6% by weight, based on the total weight of surfactant, of a fatty alcohol 7 mole ethoxylate sold commercially under the registered trademark "EMPILAN" K17. The concentrates and solutions were all stable and the solutions exhibited improved wetting agent of leaf surfaces and herbicidal activity.

EXAMPLES 54 to 103

Examples 4 to 53 were repeated with the addition of 2% based on the weight of surfactant of a chelating agent, diethylene triamine pentakis (methylene phosphonic) acid sold commercially under the Registered trademark "BRIQUEST" 543.45AS. The concentrates were stable and the solutions gave improved tolerance of hardwater.

What is claimed is:

1. A herbicidal aqueous solution comprising from 30% by weight of said solution to saturation of a water soluble glyphosate salt and from 8 to 20% by weight of said solution is surfactant, said surfactant comprising from 10 to 100% by weight based on the total weight of said surfactant of an amphoteric surfactant and from 0 to 90% by weight based on the total weight of surfactant of ether carboxylate, said solution containing less than 0.035% of sodium ion, and wherein said amphoteric surfactant has the formula $RCONH(CH_2)_n N^+ R^1{}_2 CH_2 CO_2^-$ where R is an alkyl, alkenyl or alkyl phenyl group having 6 to 20 aliphatic carbon atoms and each $R^1$ is an alkyl or hydroxyalkyl group having from 1 to 4 carbon atoms and n is an integer from 2 to 4.

2. A solution according to claim 1 wherein R is an alkyl group having from 6 to 10 carbon atoms.

3. A solution according to claim 2 wherein said amphoteric surfactant constitutes at least 30% of the total weight of the surfactant.

4. A herbicidal aqueous solution comprising:

from 30% by weight of said solution to saturation of a water soluble glyphosate salt; from 8 to 20% by weight of said solution is surfactant, said surfactant comprising from 10 to 100% by weight based on the total weight of said surfactant of an amphoteric surfactant; and from 30% to 90% by weight of ether carboxylate, based on the total weight of surfactant;

said solution containing less than 0.035% of sodium ion.

5. A herbicidal aqueous solution comprising from 30% by weight of said solution to saturation of a water soluble glyphosate salt and from 8 to 20% by weight of said solution is surfactant, said surfactant comprising from 10 to 100% by weight based on the total weight of said surfactant of an amphoteric surfactant and from 0 to 90% by weight based on the total weight of surfactant of ether carboxylate, said solution containing less than 0.035% of sodium ion, said solution further comprising a sequestrant wherein said sequestrant is an amino phosphonate of the formula $(M_2PO_3CH_2)_2N(CH_2CH_2NPO_3M_2)_n CH_2PO_3M_2$ wherein n is from 0 to 10 and M is cation such that the phosphonate is water soluble.

6. A concentrate for use in preparing an herbicidal aqueous solution comprising from 10 to 70% by weight ether carboxylate, from 20 to 80% by weight of an amphoteric surfactant which contains less than 3% of sodium chloride, from 10 to 50% by weight of a water miscible solvent.

7. A concentrate according to claim 6 comprising from 3 to 20% of a non-ionic wetting agent.

8. A concentrate according to claim 6 wherein said solvent is a polyethylene glycol having a mean molecular weight of between 90 and 600.

9. A concentrate according to claim 6 comprising 1 to 6% of a sequestrant.

10. A herbicidal aqueous solution comprising from 30% by weight of said solution to saturation of a water soluble glyphosate salt and from 8 to 20% by weight of said solution of surfactant, said solution containing less than 0.035% of sodium ion, and comprising water, glyphosate and a concentrate containing from 10 to 70% by weight ether carboxylate, from 20 to 80% by weight of an amphoteric surfactant which contains less than 3% of sodium chloride and from 10 to 50% by weight of a water miscible solvent.

11. An aqueous solution according to claim 10 wherein said solvent and from 30% by weight of said solution to saturation of a water soluble glyphosate salt is a polyethylene glycol having a mean molecular weight of between 90 and 600.

12. A herbicidal aqueous solution comprising from 30% by weight of said solution to saturation of a water soluble glyphosate salt and from 8 to 20% by weight of said solution is surfactant, said surfactant comprising from 10 to 100% by weight based on the total weight of said surfactant of an amphoteric surfactant and from 10 to 90% by weight based on the total weight of surfactant of ether carboxylate, said solution containing less than 0.035% of sodium ion; wherein said amphoteric surfactant is betaine of the formula $RR^1{}_2N^+CH_2COO^-$ where R is an alkyl or alkenyl group having 6 to 20 aliphatic carbon atoms, or an alkyl phenyl group; wherein the alkyl group has 8 to 14 aliphatic carbon atoms and each $R^1$ is an alkyl or hydroxyalkyl group having from 1 to 4 carbon atoms.

13. A solution according to claim 12 wherein R is an alkyl group having from 6 to 10 carbon atoms.

14. A solution according to claim 13 wherein said amphoteric surfactant constitutes at least 30% of the total weight of the surfactant.

* * * * *